US00PP12074P2

(12) United States Plant Patent
Zaiger et al.

(10) Patent No.: US PP12,074 P2
(45) Date of Patent: Aug. 28, 2001

(54) INTERSPECIFIC TREE NAMED 'FLAVOR GOLD'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/495,432

(22) Filed: Jan. 31, 2000

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Susan B. McCormick

(57) ABSTRACT

Our new and distinct variety of interspecific tree [*Prunus salincina*×(*Prunus salicina*×(*Prunus salicina*×*Prunus armeniaca*))×(*Prunus salicina*×*Prunus armeniaca*(], which has the following unique combination of desirable features that are outstanding in a new variety. These features of the tree and its fruit are characterized with the tree budded on 'Nemaguard' Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization:

1. Heavy and regular production of large size fruit.
2. Fruit maintaining firm flesh with a good balance between sugar and acid.
3. Fruit with excellent eating quality.
4. Fruit with good handling and shipping quality.
5. Flavor of the fruit being excellent with a blend between plum and apricot.
6. Mature fruit having good shipping quality and shelf life.
7. Having a vigorous, upright growth habit.
8. Fruit maintaining firmness on the tree approximately 2 weeks after maturity.

1 Drawing Sheet

FIELD OF INVENTION

In the field of plant genetics we conduct an extensive and continuing plant-breeding program including the origination and asexual reproduction of orchard trees, and of which plums, peaches, nectarines, apricots, cherries and interspecifics are exemplary. It is against this background of our activities that the present variety of interspecific tree was originated and asexually reproduced by us in our experimental orchard located near Modesto, Stanislaus County, California.

PRIOR VARIETIES

Among the existing varieties of plum and interspecific trees, which are, known to us, and mentioned herein, are 'Friar' Plum (non-patented), 'Autumn Giant' Plum (U.S. Plant Pat. No. 5,624), 'Red Beaut' Plum (U.S. Plant Pat. No. 2,539), Interspecific trees 'Flavor Queen' (U.S. Plant Pat. No. 7,420) and 'Flavorosa' (U.S. Plant Pat. No. 10,285).

ORIGIN OF THE VARIETY

The present new variety of interspecific [Plum×(Plum ×(PlumCot))×(PlumCot)] tree was developed by us in our experimental orchard located near Modesto, Calif., from seed of an open pollinated selected seedling [identification number 326LC131 (non-patented)], which was selected as a future parent in our breeding program. The parent 326LC131 originated as a first generation cross between two selected seedlings [field identification numbers 36ED128 (non-patented) and 7HC160 (non-patented)]. The female parent 36ED128 originated from a cross between 'Friar' Plum (non-patented) and 'Autumn Giant' Plum (U.S. Plant Pat. No. 5,624). The pollen parent 7HC160 originated as a first generation seedling from a cross of a selected seedling of an open pollinated 'Friar' Plum crossed with the plumcot (field identification number 4G1180 (non-patented)) which originated from a cross of 'Red Beaut' Plum (U.S. Plant Pat. No. 2,539) with an apricot of unknown parentage; the seedling selection from this cross was back crossed to the plumcot (4G1180). A large group of seedlings from the open pollinated interspecific tree 326LC121 were planted and maintained on their own root in our experimental orchard, during which time one seedling, which is the present variety, exhibited the distinctive desirable fruit characteristics described within and was selected in 1993 for asexual reproduction and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new and distinct variety of interspecific tree is of large size, vigorous, upright growth, a regular and productive bearer of large size, firm, clingstone fruit with excellent flavor and eating quality, having a good balance between acid and sugar with high soluble solids of 22.1° Brix. The fruit is further characterized by having a distinct flavor between plum and apricot with firm flesh, good handling and shipping quality, having relatively uniform, large size fruit throughout the tree and, in comparison to the plum selection '36ED128', which also has fruit with yellow skin color, the new interspecific fruit is larger in size, has flesh that is approximately 10° higher in Brix and is approximately 3 weeks later in maturity, in the comparison to the fruit of the interspecific selection '7HC160', which has fruit with a red blush over a yellow skin color, the new variety has larger size fruit, firmer flesh and is approximately 2 weeks later in maturity. In comparison to the fruit of the Interspecific tree 'Flavor Queen' (U.S. Plant Pat. No. 7,420), the fruit of the new variety is larger in size, has firmer flesh and is approximately 1 week later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens budded on 'Nemaguard' Rootstock (non-patented), and grown near Modesto, Calif., with color terminology (except those in common terms) in accordance with Reinhold Color Atlas by A. Kornerup and J. H. Wanscher.

Tree:

*Size.*—Large. Height and width are reduced by pruning to approximately 12 to 14 feet for economical harvesting of fruit.

*Vigor.*—Vigorous. Tree grows 5 to 7 feet in height and 4 to 5 feet in width the first growing season. Pruned to 4 to 5 feet in height and primary scaffolds selected in the first dormant season. Height and width may vary slightly with type and depth of soil, cultural practices and climatic conditions.

*Growth.*—Upright. Growth of tree becomes more spreading as the tree starts producing due to weight of crop load.

*Productivity.*—Productive. Usually sets two or more times the amount of desired fruit for normal tree crop load and fruit must be thinned and spaced to develop into desired market size. Average 35 fruit per single layer flat, minimum 12 lbs. Average 70 fruit per two-layer lug, minimum 22 lbs. Size and number of fruit depends on amount of thinning, tree spacing, soil type, cultural practices and climatic conditions.

*Bearer.*—Regular. Has set full crop load for 5 consecutive years.

*Form.*—Usually pruned to vase shape. Removing branches and leaves from the center of tree for more air movement and sunlight throughout the tree to enhance fruit coloration, and healthy growth of fruitwood.

*Density.*—Medium dense. Pruning is necessary to open tree for air movement and sunlight. Primary scaffolds with wide-angle crotches are selected to carry heavy crop load.

*Hardiness.*—Tree grown in USDA Hardiness Zone 9. Winter chilling requirement is approximately 550 hours below 45° F.

Trunk:

*Size.*—Large. Measured 19 inches in circumference at 12 inches above ground on 7 year old tree, varies with type of soil, cultural practices and climatic conditions.

*Texture.*—Medium shaggy.

*Color.*—Varies from mouse gray to hair brown (5-E-1) to (5-F-4). Varies with age of tree.

Branches:

*Size.*—Medium. Circumference averages 8 inches at 30 inches from ground.

*Texture.*—Smooth to medium rough, varies with age of growth.

*Lenticels.*—Numerous. Average number of 65 in a 4 square inch section. Small size, 3/32 inch in length, 1/32 inch in width. Size increases as branches become larger. Color — topaz to brownish yellow (4-C-5) to (4-C-6).

*Color.*—Light brown to linoleum brown (5-E-6) to (5-E-7). Varies with age of growth.

Leaves:

*Size.*—Large. Average length 6 inches. Average width 1½ inches.

*Arrangement.*—Alternate between medium length nodes.

*Form.*—Obovate.

*Apex.*—Acuminate.

*Base.*—Cuneate.

*Margin.*—Serrulate.

*Thickness.*—Medium.

*Surface.*—Upper surface — smooth. Lower surface — relatively smooth except for small ridges created by midvein with pinnate venation. Veining color — grayish yellow (2-B-4) to (2-B-6).

*Petiole.*—Average length 1 inch. Average width 1/16 inch. Grooved longitudinally. Color — surface exposed to sun brownish red (10-C-7). Surface in shaded areas grayish green (30-B-5).

*Glands.*—Number varies from 1–5. Average number 3. Globose, small size. Color — light yellow to dull yellow (3-B-4) to (3-C-4), varies with age of leaf. Located on the upper portion of the petiole and the lower portion of the leaf blade.

*Color.*—Upper surface — green to parrot green (30-E-5) to (30-E-8). Lower surface — dull green to green (29-D-5) to (29-D-7).

Flower buds:

*Size.*—Small to medium. Average length 19/64 inch. Average width 3/16 inch.

*Form.*—Plump, conical, becoming elongated with maturity.

*Color.*—White (1-A-1).

Flowers:

*Size.*—Large. Average height 9/32 inch. Average diameter 21/32 inch.

*Petal.*—Number—5, alternately arranged to sepals. Obovate, edges vary from smooth to slightly scalloped. Apex — rounded. Base — narrows to point of attachment. Surface — sinuate, cupped. Texture — smooth, glabrous. Color — upper and lower surface white (1-A-1).

*Sepals.*—Number 5 — alternately arranged to petals. Shape — triangular, slightly rounded apex. Average length 9/64 inch. Average width 5/64 inch at base of attachment. Color — upper surface, light green (29-A-4). Lower surface — light green (29-A-4). Both surfaces glabrous.

*Stamens.*—Number per flower varies from 31 to 41. Average number 34. Filament length — 13/64 inch. Filament color — white (1-A-1). Anther color — golden yellow to brownish yellow (5-B-7) to (5-C-6).

*Pistil.*—Number — 1. Average length 3/16 inch. Color — greenish white (30-A-2). Stigma positioned approximately 5/64 inch below anthers.

*Aroma.*—Slight fragrance.

*Pollen.*—Present, pollen sacs full. Color — pale yellow to yellow (3-A-3) to (3-A-5). Self sterile, pollenizer required. Under controlled conditions, present test indicate 'Flavorosa' (U.S. Plant Pat. No. 10,285) may be a suitable pollenizer.

*Blooming period.*—Date of First Bloom Feb. 20, 1999. Date of Last Bloom Mar. 2, 1999. Varies slightly with climatic conditions.

Fruit:

*Maturity when described.*—Firm (shipping ripe).

*Date of first picking.*—Jul. 30, 1999.

*Date of last picking.*—Aug. 8, 1999.

*Size.*—Average diameter axially 2½ to 2⅝ inches. Average transversely in suture plane 2½ to 2⅝ inches. Average weight 150.5 grams. Average weight varies slightly with fertility of the soil, number of fruit on tree and climatic conditions.

*Form.*—Nearly globose, slightly flattened at stem end.

*Suture.*—Shallow, extends from base to apex.

*Ventral surface.*—Nearly smooth, slightly flattened.

*Apex.*—Usually rounded, slightly retuse on some fruit.

*Base.*—Retuse.

*Cavity.*—Shallow, small, slightly elongated in suture plane. Average depth 3/16 inch. Average breadth ⅜ inch.

Skin:

*Thickness.*—Medium.

*Texture.*—Medium thickness, very smooth, tenacious to the flesh.

*Bloom.*—Moderate.

*Tendency to crack.*—Very slight.

*Color.*—Lemon yellow to mustard yellow (3-B-8) to (3-C-8). Very slight pale red blush (11-A-4) on areas of some fruit exposed to sun.

Stem:

*Size.*—Average length ⅝ inch. Average diameter ⅛ inch.

*Color.*—Yellowish brown to light brown (5-D-5) to (5-D-8).

Flesh:

*Ripens.*—Evenly.

*Texture.*—Firm, meaty.

*Fibers.*—Few, small, tender.

*Aroma.*—Slight.

*Eating quality.*—Excellent.

*Flavor.*—Sweet, good balance between sugar and acid.

*Juice.*—Moderate, sweet, enhances flavor.

*Brix.*— 22.1°.

*Color.*—Light yellow to yellow (4-A-4) to (4-A-6). Pit cavity — yellow to grayish yellow (4-A-5) to (4-B-5).

Stone:

*Type.*—Clingstone.

*Size.*—Medium. Average length 1 inch. Average width 23/32 inch. Average thickness ⅜ inch.

*Form.*—Varies from ovoid to obovoid.

*Base.*—Usually straight, varies from straight to slightly retuse.

*Apex.*—Acuminate.

*Surface.*—Very lightly pitted throughout, usually three or four small narrow ridges extending from base approximately ⅓ distance toward apex. One shallow furrow running on each side of stone near suture.

*Sides.*—Equal to unequal, some stones are slightly larger on one side.

*Tendency to split.*—None.

*Color.*—Tan to light brown (5-C-6) to (5-D-6), when dry.

Use: Market. Local and long distance.

Keeping quality: Good. Fruit stored for 3 weeks at 38° to 42° F. showed no internal browning or wooliness of flesh.

Shipping quality: Good. Minimal scarring or bruising of skin or flesh during packing or shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics, with abnormal fungus, bacterial, virus, or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, upright growth and being a productive and regular bearer of large size, yellow flesh fruit with excellent flavor and eating quality; the fruit is further characterized by having firm flesh with good handling and shipping quality, having high soluble solids (Brix 22.1°) and, in comparison to the interspecific tree 'Flavor Queen' (U.S. Plant Pat. No. 7,420), the fruit of the new variety has firmer flesh, is larger in size and is approximately 1 week later in maturity.

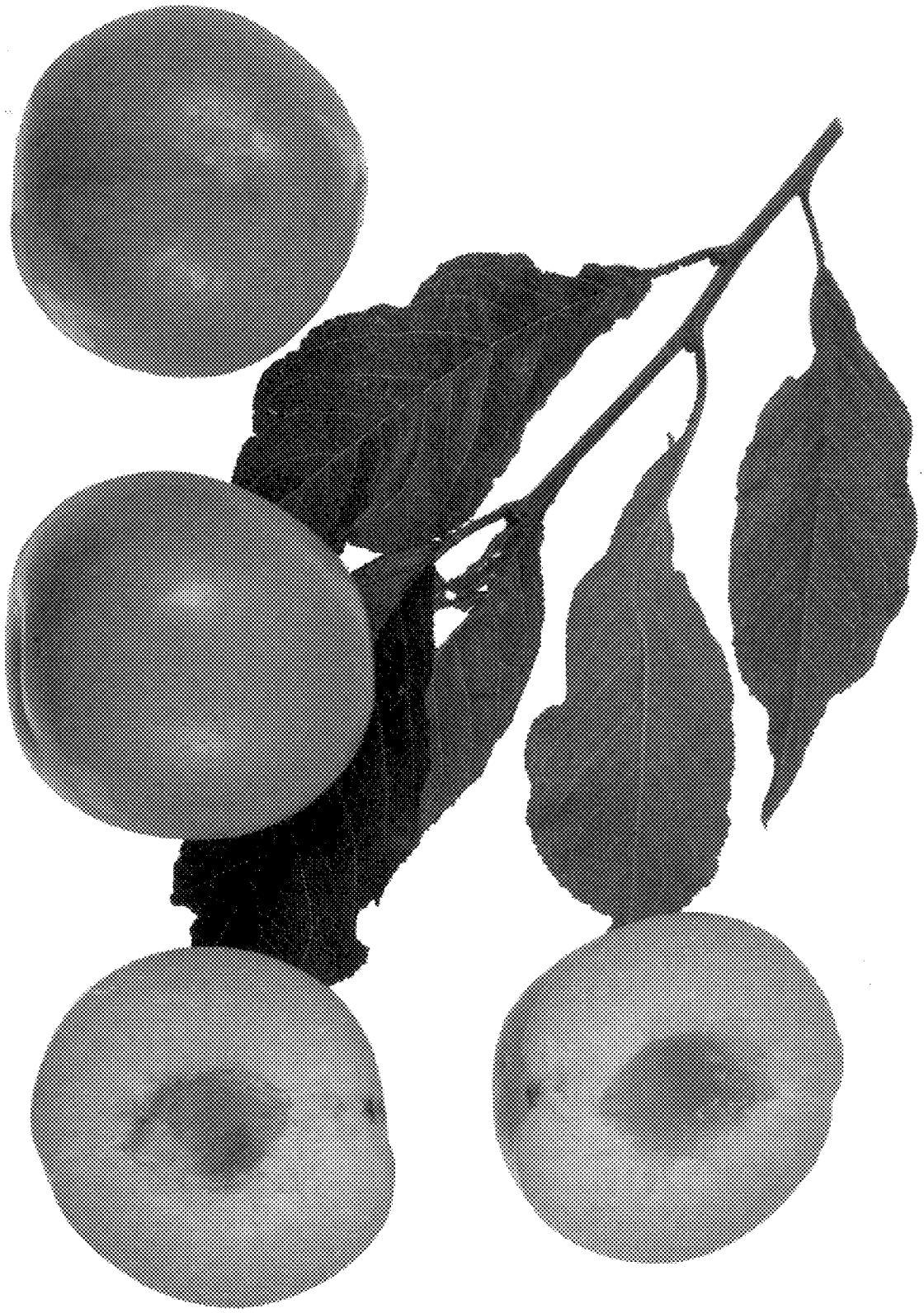

* * * * *